(12) United States Patent
Hammond et al.

(10) Patent No.: US 7,361,493 B1
(45) Date of Patent: Apr. 22, 2008

(54) PRODUCTION OF UROKINASE IN A THREE-DIMENSIONAL CELL CULTURE

(75) Inventors: Timothy G. Hammond, New Orleans, LA (US); Patricia L. Allen, New Orleans, LA (US)

(73) Assignees: The United States of America as represented by the Secretary of the Department of Veterans Affairs, Washington, DC (US); Tulane University, New Orleans, LA (US)

( * ) Notice: Subject to any disclaimer, the term of this patent is extended or adjusted under 35 U.S.C. 154(b) by 61 days.

(21) Appl. No.: 11/139,102

(22) Filed: May 26, 2005

Related U.S. Application Data

(60) Provisional application No. 60/574,756, filed on May 26, 2004.

(51) Int. Cl.
*C12N 9/12* (2006.01)

(52) U.S. Cl. ...................... 435/194; 435/212

(58) Field of Classification Search ................ 435/194, 435/212
See application file for complete search history.

(56) References Cited

U.S. PATENT DOCUMENTS

| | | | |
|---|---|---|---|
| 4,640,835 A | 2/1987 | Shimizu et al. | |
| 4,945,203 A * | 7/1990 | Soodak et al. | 219/121.64 |
| 5,747,291 A | 5/1998 | Steffens et al. | |
| 6,506,598 B1 | 1/2003 | Andersen et al. | |
| 2005/0064443 A1 | 3/2005 | Goodwin et al. | |

FOREIGN PATENT DOCUMENTS

EP 0200451 12/1993

OTHER PUBLICATIONS

Cowger et al., "Expression of Renal Cell Protein Markers is Dependent on Initial Mechanical Culture Conditions," J. Appl. Physiol., 92: 691-700 (Feb. 2002).
Dichek et al., "Enhanced In Vivo Antithrombotic Effects of Endothelial Cells Expressing Recombinant Plasminogen Activators Transduced With Retroviral Vectors," CIRCULATION, 93(2): 301-309 (1996).
Gimbrone, "Vascular Endothelium, Hemodynamic Forces, and Atherogenesis," Am. J. of Pathology, 155(1): 1-5 (Jul. 1999).
Guo et al., "A Hydrodynamic Mechanosensory Hypothesis for Brush Border Microvilli," Am. J. Physiol. Renal Physiol., 279: F698-F712 (2000).
Hammond et al., "Optimized Suspension Culture: The Rotating-Wall Vessel," Am. J. Physiol. Renal Physiol., 281: F12-F25 (2001).
Harbour et al., "Process Development for Hybridoma Cells," Adv. in Biochem. Eng. Biotechnol., 37: 1-40 (1988).
Hu et al., "Pilot Production of u-PA with Porous Microcarrier Cell Culture," CYTOTECHNOLOGY, 33: 13-19 (2000).
Jo et al., "Performance Study of Perfusion Cultures for the Production of Single-Chain Urokinase-Type Plasminogen Activator (scu-PA) in a 2.5 l Spin-Filter Bioreactor," Bioprocess Eng., 19: 363-372 (1998).
Jones et al., "Bioprocess Considerations in Using Animal Cell Culture," 13 pp. (Apr. 7, 2003).
Joshi et al., "Animal Cell Biotechnology," http://www.virology.net/Articles/mass.html, 16 pp. (first visited Jan. 21, 2004).
Korenaga et al., "Negative Transcriptional Regulation of the VCAM-1 Gene by Fluid Shear Stress in Murine Endothelial Cells," American J. Physiol., 273: C1506-C1515 (Nov. 1997).
Mahoney et al., "Cell Adhesion Regulates Gene Expression at Translational Checkpoints in Human Myeloid Leukocytes," Proc. Natl. Acad. Sci., 98(18): 10284-10289 (Aug. 28, 2001).
Stathopoulos et al., "Shear Stress Effects on Human Embryonic Kidney Cells In Vitro," Biotech. and Bioeng., 27: 1021-1026 (Jul. 1985).
Xiao et al., "High Density and Scale-Up Cultivation of Recombinant CHO Cell Line and Hybridomas with Porous Microcarrier Cytopore," CYTOTECHNOLOGY, 30: 143-147 (1999).
"Cytodex™ 1, Cytodex 3," Amersham Biosciences, 18-1119-79, Edition AB, 4 pp. (2002).

* cited by examiner

*Primary Examiner*—Jon Weber
*Assistant Examiner*—Tiffany Gough
(74) *Attorney, Agent, or Firm*—Klarquist Sparkman, LLP

(57) ABSTRACT

Embodiments of a method for the production of human urokinase are disclosed. Also disclosed are embodiments of a cell culture well-suited for use with the disclosed method. The method involves culturing urokinase-producing cells, such as immortalized human renal cells, in a cell culture. The cell culture comprises microcarrier structures and a tissue culture medium. The urokinase production is allowed to occur while the cell culture remains relatively static, i.e., the cell culture is not substantially mixed.

22 Claims, 8 Drawing Sheets

PRODUCTION OF UROKINASE IN A THREE-DIMENSIONAL CELL CULTURE

CROSS REFERENCE TO RELATED APPLICATION

This claims the benefit of U.S. Provisional Application No. 60/574,756, filed May 26, 2004, which is incorporated herein by reference.

FIELD

This disclosure relates to cell culture conditions for the production of polypeptides, specifically to cell culture conditions for the production of urokinase.

BACKGROUND

In the human body, blood clots form and dissolve by dynamic processes. Blood clots primarily comprise fibrin, which can be broken down by plasmin in a process known as fibrinolysis. Plasmin is derived from plasminogen, which is formed in the liver and flows freely in the circulatory system. The conversion of plasminogen to plasmin is catalyzed by plasminogen activators, such as urokinase. Urokinase is produced in the kidney and is found naturally in the blood and urine. It circulates in an inactive single-chain form and is converted into an active two-chain form in the presence of plasmin.

The initiation of fibrinolysis is useful for a variety of medical treatments, such as the treatment of patients suffering from acute vascular diseases. Since urokinase causes the initiation of fibrinolysis, it has significant medical utility. Urokinase is especially effective for the treatment of vascular diseases characterized by thrombosis or thromboembolism. In addition to its medical utility for breaking down existing blood clots, urokinase also is useful for inhibiting the formation of new blood clots.

Methods for the production of human urokinase that rely on the isolation of urokinase from blood or urine have been described (see, for example, U.S. Pat. No. 5,156,967). Other conventional methods rely on recombinant DNA techniques (see, for example, U.S. Pat. No. 5,112,755). Unfortunately, most conventional techniques for the production of urokinase are complex and expensive and are not designed to produce large quantities of urokinase. Thus, a need remains for methods for producing urokinase.

SUMMARY

Embodiments of a method are disclosed for the production of human urokinase by culturing cells. Embodiments of a specialized cell culture for use with this method also are disclosed. The method can include culturing urokinase-producing cells in a cell culture comprising a plurality of microcarrier structures and a tissue culture medium. In contrast to conventional methods, the cells can be cultured without substantial mixing for a period, such as a period greater than about three hours. In one example, the cells are cultured under conditions with minimal shear stress, such as shear stress that is less than about 0.1 dynes/cm$^2$. Cells cultured according to the disclosed method produce urokinase, which can be isolated from the cell cultures and purified.

The urokinase-producing cells can be, for example, human renal cells or immortalized human renal cells. The plurality of microcarrier structures can include a variety of three-dimensional structures, such as beads and/or rods. In some embodiments, the plurality of microcarrier structures includes glass beads and/or microcarrier structures comprising a dextran core coated with collagen. The ratio of cells to microcarrier structures in the cell culture can be, for example, greater than about 25:1 and less than about 500:1.

In some embodiments of the disclosed method, the cell culture is contained within a vessel. The vessel, for example, can be a flexible bag, such as a TEFLON® bag. Some suitable vessels have interior surfaces that are resistant to cell attachment. To promote optimal cell culture conditions without the need to supply gases from an external source, some vessels used with embodiments of the disclosed method are substantially $CO_2$-retaining and substantially $O_2$-permeable. For example, some vessels allow a sufficient amount of oxygen to diffuse into the cell culture to replace the oxygen consumed by the urokinase-producing cells and also retain at least a portion of the carbon dioxide produced by the urokinase-producing cells, so as to maintain an elevated concentration of carbon dioxide (relative to air) within the cell culture during the production of urokinase.

DETAILED DESCRIPTION

I. General Abbreviations

Figure 1:
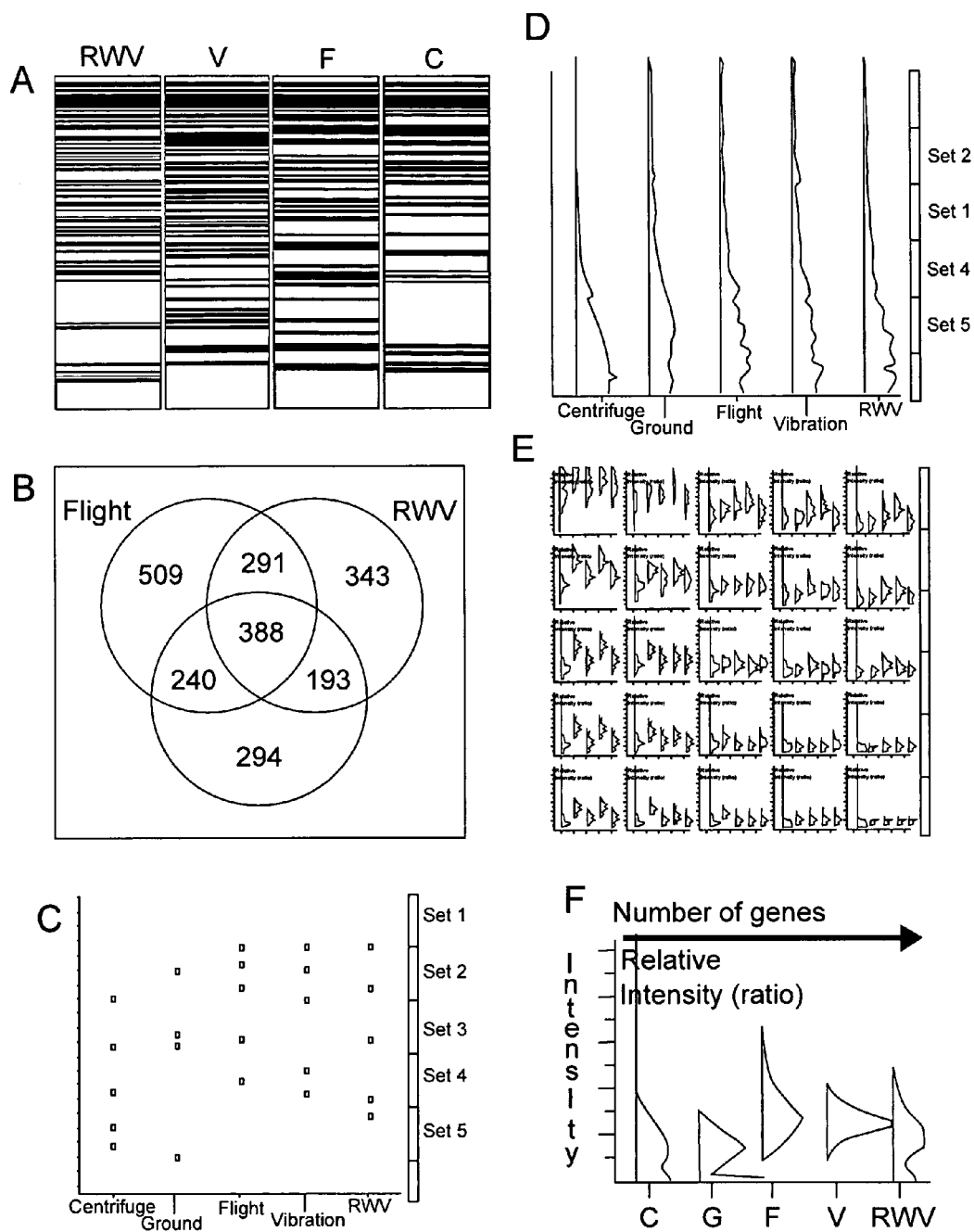
FIG. 1A is a comparison of gene expression levels of human renal cortical cells subjected to different mechanical culture conditions. The figure was generated using Gene-Spring Software (Silicon Genetics, Palo Alto, Calif.). The same genes are shown in each column as bars from top to bottom with dark grey intensity representing the degree of decrease in each gene and light grey intensity representing the degree of increase in each gene.
FIG. 1B is an example of a Venn diagram used to produce gene lists corresponding to the gene expression levels of human renal cortical cells subjected to different mechanical culture conditions.
FIG. 1C is a principal component analysis gene cluster diagram illustrating gene expression for human renal cortical cells subjected to different mechanical culture conditions.
FIG. 1D is a K-means cluster diagram illustrating gene expression for human renal cortical cells subjected to different mechanical culture conditions.
FIG. 1E is a self organizing map gene cluster diagram illustrating gene expression for human renal cortical cells subjected to different mechanical culture conditions.
FIG. 1F is a close-up of a portion of the diagram illustrated in FIG. 1E.

BBS: N,N-bis(2-hydroxyethyl)-2-aminoethanesulfonic acid and buffered saline
BCA: BioServe culture apparatus
BN: binucleated
BSA: bovine serum albumin
BUN: blood urea nitrogen
C: centrifugation
cm: centimeter
CHO: Chinese hamster ovary
dB/oct: decibel per octave
DMEM: Dulbecco's modified eagle's medium
ds: double stranded
ELISA: enzyme-linked immunosorbent assay
F: space shuttle flight
g: acceleration due to gravity
G: ground control
iNOS: nitric oxide synthase
Hz: hertz
M: molar
MM: mismatched
ml: milliliter
mmHG: millimeter mercury
nM: nanomolar
ng: nanogram
PCA: principal component analysis
PKC: protein kinase C
PM: perfectly matched
PTH: parathyroid hormone
RIA: radioimmunoassay
RWV: rotating wall vessel
SOM: self-organizing map
SV40 Tag: simian virus 40 large T antigen
μg: microgram
μl: microliter
μm: micrometer
t-PA: tissue plasminogen activator
u-PA: urokinase-type plasminogen activator
V: vibration II. Gene Abbreviations 25-OH Vit D3 1-a-OHase: 25-hydroxy vitamin D3 1-alpha hydroxylase
ABC1: zinc finger protein 217
ALK-1: human activin receptor-like kinase 1
BAI1-associated protein: brain-specific angiogensis inhibitor precursor associated protein 1
BLR1: burkitt lymphoma receptor 1, GTP-binding protein
CDK8: cyclin-dependent kinase 8
CHK1: protein kinase
COL4A2: collagen, type IV, alpha 2
COL11A2: collagen, type XI, alpha 2
CRABP-II: retinoic acid-binding protein II
CYB5: cytochrome B5
CYP1: cytochrome P450, subfamily I (aromatic compound-inducible), polypeptide 1
CYP1A2: cytochrome P450, subfamily I (aromatic compound-inducible), polypeptide 2
CYP2A3: cytochrome P450, subfamily IIA (phenobarbital-inducible), polypeptide 3, coumarin resistance, coumarin 7-hydroxylase, cytochrome P450, cytochrome P450 IIA3
CYP2C: cytochrome P450, subfamily IIC (mephenyloin 4-hydroxylase), polypeptide 9
CYP4F: cytochrome P450, subfamily IVF, polypeptide 3 (leukotriene B4 omega hydroxylase)
DAGK3: diacylglycerol kinase, gamma (90 kD)
DDR3: death domain receptor 3
DP-1: polyosis locus
E2F-5: E2F transcription factor 5, p130-binding
EEF1A: eukaryotic translation elongation factor 1, alpha 1
EIF2: eukaryotic translation initiation factor 2, subunit 3 (gamma, 52 kD)
EPHA5: EHK-1 receptor tyrosine kinase
EPOR: erythropoietin receptor precursor
ERCC1: excision repair protein
ERK1: mitogen-activated protein kinase 3, erk1 gene, protein-serine/threonine kinase
FAP: fibroblast activation protein, alpha
GAPDH: glyceraldehyde-3-phosphate dehydrogenase
GATA-2: human transcription factor GATA-2
GMP: 3',5'-cyclic guanidine monophosphate phosphodiesterase
GRF-1: glucocorticoid receptor repression factor 1
$HC_{7-1}$: eukaryotic translation elongation factor 1, alpha 1
HEK2: protein tyrosine kinase receptor
HEK7: human receptorprotein-tyrosine kinase
HEK11: receptor protein-tyrosine kinase, EPH-like receptor protein-tyrosine kinase
HIF-1a: hypoxia-inducible factor 1, alpha
HSP90-b: heat shock 90 kD protein 1, beta
HSP110: heat shock protein 110 kDa
HSPA1L: HSP70 gene; heat shock protein or heat shock protein 70 testis variant
HSXIAPAF1: XIAP associated factor 1
IEX-1: radiation-inducible immediate early response 3
IGFBP-2: insulin-like growth factor binding protein 2
IFNB: interferon, beta 1, fibroblast, signal peptide
IFNG: interferon, gamma
JAK1: protein tyrosine kinase
KIF3X: kinesin family related motor protein
$KBF_1$: H-2K binding factor 2
KIP: cdk-inhibitor, alternative splicing product, Beckwith-Wiedemann syndrome or DNA-dependent protein kinase catalytic subunit-interacting protein 2
MEK2: ERK activator kinase
MAPKK1: mitogen-activated protein kinase 1
MART-1: mono-ADP-ribosyltransferase
MLC-3: myosin light chain 3, mid ventriculatar chamber type
NEC2: neuroendocrine convertase 2
NF-kappa-B: nuclear factor kappa-beta
NFKB3: NF-kappa-B p65 subunit, transcription factor
NF1: neurofibromin isoform lacking a domain related to GTPase-activating protein, NF1 protein isoform, nuerofibromatosis type 1, leukemia, juvenile myelomonocytic, or nuclear factor I/X (CCAAT-binding transcription factor)

(NF1 A), or Zinc finger protein 162, SF1-Bo isoform, splicing factor SF1 (ZNF162)

NPAT: housekeeping gene

NRAMP1: natural resistance associated macrophage protein 1

P kinase C, iota: protein kinase C, iota

P450IIE: P450, subfamily IIE (ethanol-inducible)

P450IIF: P450, subfamily IVF, polypeptide 2

P450IIA3: P450, subfamily IIA (phenobarbital-inducible), polypeptide 3

P450IIIA: P450, subfamily IIIA (niphedipine oxidase)

P450IVF: P450, subfamily IVF

P450XIB: P450, subfamily XIB (steroid 11-beta-hydroxylase), polypeptide 1

PEX1: perixome biogenesis factor 1

PKCI-1: histidine triad nucleotide-binding protein, protein kinase C inhibitor

PKCM: protein kinase C mu

RABA3: ras oncogene, guanidine triphosphate binding protein

RAD6B: HHR6B (Human homologue of yeast RAD 6), ubiquitin-conjugating enzyme E2B (RAD6 homolog)

RAS2A: RAS oncogene family member 2A

RP1: compliment C4B precusor

SAPK4: mitogen-activated protein kinase 13 producing serine/theorine protein kinase SKIP: skeletal muscle and kidney enriched inositol phosphatase SMA5: beta glucoronidase pseudogene SMAD2: mothers against decapentaplegic, drosophila protein homolog SMAD5: mothers against decapentaplegic, drosophila homolog 5

SP1: transcription factor SP 1

SYK: spleen tyrosine kinase $TCF_3$: transcription factor 3 (E2A immunoglobulin enhancer binding factors E12/E47), leukemia, acute lymphoblastic TEF-1: transcriptional enhancer factor TFIIB: transcription factor IIB3

TGF-beta 1: transforming growth factor beta 1

TGF-beta 3: transforming growth factor beta 3

TSP1: testis specific protein, Y-linked (TSPY) or Tetraspan 1 (TSPAN-1) or Tetraspan 5 (TSPAN-5)

TRAF6: TNF receptor-associated factor 6

VLA1: integrin, alpha 2 (CD49B, alpha 2 subunit of VLA-2 receptor) or very-long-chain acyl-CoA synthetase III. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA is synthesized in the laboratory by reverse transcription from messenger RNA extracted from cells.

Cell Culture: An in vitro environment in which cells are grown on a medium. A "cell culture medium" or a "tissue culture medium" is a synthetic set of culture conditions with the nutrients necessary to support the growth (expansion) of a specific population of cells. In one embodiment, the cells are urokinase-producing cells. A medium generally includes a carbon source, a nitrogen source, and a buffer to maintain pH. In one embodiment, the growth medium contains a minimal essential media, such as DMEM, supplemented with various nutrients to enhance cell growth. Additionally, the minimal essential media may be supplemented with additives such as horse, calf, or fetal bovine serum. Antibiotics and fungicides also can be included to deter the growth of unwanted bacteria or fungi.

Culture Period: The entire period during which live cells exist in a cell culture.

DNA: Deoxyribonucleic acid. DNA is a long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon also is used for the corresponding (and complementary) sequences of three nucleotides in the mRNA into which the DNA sequence is transcribed.

Enhanced Urokinase Production: Urokinase production by cells in a cell culture that is increased in quality or quantity relative to typical urokinase production achieved with conventional cell culture techniques. In several examples, enhanced urokinase production can be urokinase production from about 50 ng/ml to about 500 ng/ml, or from about 60 ng/ml to about 500 ng/ml, such as from about 70 ng/ml to about 500 ng/ml after about 24 hours of culture.

Expand: A process by which the number or amount of cells in a cell culture is increased due to cell division. Similarly, the term "expansion" or "expanded" refers to this process. The terms "proliferate," "proliferation" or "proliferated" may be used interchangeably with the words "expand," "expansion," or "expanded."

Gene: A DNA sequence that comprises control and coding sequences necessary for the production of a polypeptide or protein. The polypeptide can be encoded by a full-length coding sequence or by any portion of the coding sequence in some embodiments, so long as at least a portion of the desired activity of the polypeptide is retained. A "foreign" or "heterologous" gene sequence is any nucleic acid that is introduced into the genome of an animal by experimental manipulations. This can include gene sequences found in that animal so long as the introduced gene contains some modification (for example, a point mutation, the presence of a selectable marker gene, a non-native regulatory sequence, or a native sequence integrated into the genome at a non-native location, etc.) relative to the naturally-occurring gene.

Gene Expression: Transcription of DNA into mRNA and production of protein from this mRNA.

Immortalized: An immortalized cell is a cell that can grow and reproduce indefinitely in culture.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Microcarrier Structures: Small, solid structures introduced into a cell culture to facilitate the growth, viability, and/or activity of the cells in the cell culture. Microcarrier structures can affect the cell culture in several ways, including increasing the surface area available to the cells. Exemplary microcarrier structures are glass beads, polystyrene beads, polypropylene beads, and dextran beads. The beads are small, usually non-elongated, three-dimensional structures presenting a surface (such as a closed continuous surface or a porous surface) and having a variety of cross-sectional shapes (such as a circle, a triangle, a square, a cone, etc.). The microcarriers can be coated with a matrix, such as a matrix comprising collagen (for example, types I or V), fibrin, laminin, and/or urokinase receptor antibodies.

Normal Gravity: The unadulterated gravitational force experienced by objects on the Earth's surface.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Protein: A polymer, also termed "polypeptide," in which the monomers are amino acid residues which are joined together through amide bonds, regardless of length or post-translational modification (for example, glycosylation or phosphorylation). When the amino acids are alpha-amino acids, either the L-optical isomer or the D-optical isomer can be used, the L-isomers being preferred. In one embodiment, the polypeptide is urokinase.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter optionally also includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (for example, metallothionein promoter) or from mammalian viruses (for example, the retrovirus long terminal repeat; the adenovirus late promoter; the vaccinia virus 7.5K promoter). Promoters produced by recombinant DNA or synthetic techniques also may be used. A polynucleotide can be inserted into an expression vector that contains a promoter sequence that facilitates the efficient transcription of the inserted genetic sequence of the host. The expression vector typically contains an origin of replication, a promoter, as well as specific nucleic acid sequences that allow phenotypic selection of the transformed cells.

A promoter is "operably linked" to another nucleic acid molecule if it can drive expression of the nucleic acid. For example, a promoter operably linked to a nucleic acid encoding urokinase can be used for the production of urokinase in a cell.

Purified: The term "purified" does not require absolute purity; rather, it is intended as a relative term. Thus, for example, a purified protein preparation is one in which the protein referred to is more pure than the protein in its natural environment within a cell. A substantially purified protein is at least 60%, 70%, 80%, 90%, 95% or 98% pure (isolated). Thus, in one specific, non-limiting example, a substantially purified protein is at least 90% free of other proteins or cellular components.

Recombinant: A recombinant nucleic acid is one that has a sequence that is not naturally occurring or has a sequence that is made by an artificial combination of two otherwise separated segments of sequence. This artificial combination often is accomplished by chemical synthesis or, more commonly, by the artificial manipulation of isolated segments of nucleic acids, for example, by genetic engineering techniques.

Static: A culture condition characterized by a lack of substantial mixing. For example, a static cell culture can have a shear stress less than about 0.4 dyne/cm$^2$, such as less than about 0.1 dynes/cm$^2$ or less than about 0.05 dynes/cm$^2$. In some examples, the static culture is characterized by an absence of mixing, except for changing the media (for example, by intermittently adding nutrients). For example, the culture medium is not substantially continuously agitated or fluidized to mix the microcarrier structures and culture nutrients. For example, in some embodiments of the disclosed method, there is no agitation by a stirring device, such as a magnetic stirrer, a rotor or a roller.

Static Period Any period during which a cell culture is allowed to exist in a substantially static condition. The continuity of the static period is not necessarily undermined by periodic spikes in the shear stress of the culture media.

Substantial Mixing: Substantial mixing is agitation of the cell culture, such as agitation designed to promote the delivery of medium components to cells in the cell culture. Cell cultures that include a spinner bar in motion, and cell cultures that are rotated, generally have substantial mixing. In an additional example, substantial mixing is a set of cell culture conditions wherein the sheer stress is greater than about 0.4 dyne/cm$^2$, such as greater than about 0.8 dynes/cm$^2$ or greater than about 1 dyne/cm$^2$.

Transfected: Transfected cells are cells that have had foreign DNA molecules introduced.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Urokinase: An enzyme, also known as plasminogen activator, that enzymatically activates plasminogen. Urokinase is a proteinase that converts plasminogen to plasmin by cleavage of a single (usually Arg-Val) bond in plasminogen.

Unlike tissue plasminogen activator (t-PA) or prourokinase (single chain urokinase-type plasminogen activator) urokinase does not require fibrin for activity. Urokinase can be altered (for example, by chemical derivatization, mutations such as conservative substitutions, or incorporation into a fusion protein) while retaining its natural biological activity. Examples of such urokinase variant molecules are disclosed in U.S. Pat. No. 4,640,835; U.S. Pat. No. 5,747,291; European Patent No. EP0200451; W. F. Bennett, N. F. Paoni, B. A. Keyt, D. Botstein, A. J. Jones, L. Presta, F. M. Wurm, M. J. Zoller, *High Resolution Analysis of Functional Determinants on Human Tissue-Type Plasminogen Activator*, 266(8) J. Biol. Chem. 5196-201 (1991); and D. Collen and H. R. Lijnen, *Tissue-type Plasminogen Activator: a Historical Perspective and Personal Account*, 2(4) J. of Thrombosis and Haemostasis 541-6 (2004). All such variants, derivatives, fusion proteins and other modified forms are included in the term "urokinase" unless context clearly indicates otherwise.

Naturally occurring urokinase is produced by the kidney and excreted in the urine in vivo. Urokinase is used therapeutically to induce therapeutic thrombolysis.

Urokinase-Producing Cells: Cells that can produce urokinase. Several examples of urokinase-producing cells are human renal cells, immortalized human renal cells, and cells (such as Chinese hamster ovary cells) transformed with a nucleic acid encoding urokinase.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector also can include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications other than patents mentioned herein are incorporated by reference in their entirety. In case of conflict, the present specification, including explanations of terms, will control. In addition, the materials, methods, and examples are illustrative only and not intended to be limiting.

IV. Production of Urokinase in a Three-Dimensional Cell Culture

Described herein are embodiments of a method for the production of human urokinase, as well as embodiments of a cell-culture device. The disclosed embodiments are based, in part, on the surprising discovery that urokinase production is enhanced when urokinase-producing cells are cultured without substantial mixing, at normal gravity and with microcarrier structures.

A. Culture without Substantial Mixing

Conventional cell-culture techniques typically involve some mixing of the cell culture. The mixing is intended to distribute nutrients and oxygen and thereby enhance the productivity of the cells. Mixing can be accomplished, for example, by introducing a magnetic stir bar into the cell culture. However, excessive mixing can damage cells, especially animal cells, which lack a cell wall (see, for example, R. S. Cherry, *Animal Cells in Turbulent Fluids: Details of the Physical Stimulus and the Biological Response*, 11(2) Biotechnol Adv. 279-99 (1993)). Somewhat gentler mixing can be accomplished by slowly rotating the cell culture, for example, in a roller bottle rotated at a rate of about 5 to 60 rotations per hour. Another approach to mixing the cell culture is to use a continuously flowing media. In a perfusion culture, new media is continuously introduced as used media is removed. All of these culture systems include conditions wherein substantial mixing of the medium components occurs. Generally, it is believed that substantial mixing increases the production of biological components, such as proteins, by cultured cells.

Prior to the experiments associated with this disclosure, there was no reason to expect that urokinase production would differ from the production of other biological agents. It is disclosed herein that urokinase production is inhibited by substantial mixing of the cell culture. The embodiments of the method described herein for urokinase production involve allowing the urokinase-producing cells to produce urokinase during a static period characterized by a lack of substantial mixing. The urokinase-producing cells can be mixed before and/or after the static period without compromising the enhanced urokinase production achieved during the static period. During the static period, the cells generally are immobilized or stationary, and an intentional effort is made to avoid mixing. Thus, substantial mixing does not occur, wherein the absence of substantial mixing is sufficient to enhance urokinase production in the culture medium.

One way to quantify the degree of mixing is to measure the shear stress of the cell-culture media. Shear stress can be measured easily with a rheometer (see, for example, U.S. Pat. No. 6,655,194). To achieve enhanced urokinase production, the shear stress of the cell-culture media during substantially all of the static period typically is less than the shear stress of the cell-culture media in conventional cell cultures used for the production of urokinase. Shear stress data for conventional cell cultures can be found, for example, in N. L. Cowger et al., *Expression of Renal Cell Protein Markers is Dependent on Initial Mechanical Culture Conditions*, 92 J. APPL. PHYSIOL. 691-700 (2002); T. G. Hammond and J. M Hammond, *Optimized Suspension Culture—The Rotating Wall Vessel*, 281 μM. J. RENAL PHYSIOL. at F12 (2001); M. A. Gimbrone Jr., *Vascular Endothelium, Hemodynamic Forces, and Atherogenesis*, 155 AM. J. PATHOL 1-5 (1999); and P. Guo et al., *A Hydrodynamic Mechanosensory Hypothesis for Brush Border Microvilli*, 280 AM. J. PHYSIOL. at C962-9 (2001), each of which is incorporated herein by reference. In some embodiments of the disclosed method, the shear stress of the cell-culture media during substantially all of the static period is less than about 0.4 dyne/cm$^2$, such as less than about 0.1 dynes/cm$^2$ or less than about 0.05 dynes/cm$^2$.

Although generally it is important to maintain the shear stress of the cell-culture media at a low level, periodic spikes in the shear stress will not necessarily inhibit the enhanced production of urokinase. These spikes may be caused, for example, by periodic handling of the cell culture (such as to feed the cells or to supplement the medium with additives), ambient vibration (such as air movement), convection, or other incidental mixing. Aside from incidental movement, mixing is avoided and, in particular, intentional agitation or mixing of the medium is not performed. Therefore, any incidental spikes of movement are very brief and transient. Generally the culture is maintained as a stationary system, without substantial mixing.

The static period can be any period during which the urokinase-producing cells in a cell culture exhibit enhanced urokinase production. For example, the static period can be a period greater than about 1 hour, such as a period greater than about 2 hours and less than about 72 hours or a period greater than about 10 hours and less than about 48 hours.

B. Culture at Normal Gravity

In the examples detailed below, several cell culture conditions were investigated for their effect on gene expression. Among these cell culture conditions was actual microgravity achieved in space and simulated microgravity achieved in a rotating wall vessel. Actual and simulated microgravity were not found to enhance the production of urokinase. Thus, in one example, the static period is characterized by normal gravity forces acting on the cell culture in addition to a lack of substantial mixing.

C. Culture with Microcarrier Structures

Some embodiments of the disclosed method involve the use of microcarrier structures in the cell cultures. Microcarrier structures can be any solid, physical structures used to modify cell cultures to promote cell growth, viability, and/or activity. For example, these structures can be used to increase the surface area available to cells in a cell culture and thereby increase the number of cells that can be cultured in a specified volume. In some embodiments, the presence of microcarrier structures makes the cell culture more closely resemble the native environment of the cells being cultured. For example, some cells prefer to adhere to surfaces. These cells often respond positively to the presence of microcarrier structures because microcarrier structures create a three-dimensional surface in the cell culture and thereby provide greater surface area within the cell culture. In some embodiments, microcarrier structures also promote the optimum spacing of the cells. Certain cells exhibit advantageous characteristics when they are situated a certain distance from other cells in the cell culture. Without being bound by theory, this distance can be manipulated by modifying the size of the microcarrier structures and/or by modifying the ratio of cells to microcarrier structures. The influence of cell spacing may be related to the diverse interactions between cells, including the chemical signals passed between cells. Spacing also can promote the distribution of oxygen and nutrients. Some or all of the above factors, among others, may be responsible for the positive effect of microcarrier structures on the production of urokinase, as observed in the experiments associated with this disclosure.

In general, microcarrier structures can be any structures introduced into a cell culture that facilitate the growth, viability, and/or activity of cells in that culture. Microcarrier structures can take any form, but typically are spherical or cylindrical. Other examples of microcarrier structures include conical, frustoconical, pyramidal, square, rectangular, and ovoid structures. Some microcarrier structures also have internal pores or surface indentations that further increase the surface-area-to-volume ratio.

Microcarrier structures of various sizes are useful for the enhanced production of urokinase. The individual microcarrier structures in a batch of microcarrier structures typically are not of uniform size. A batch of microcarrier structures is best characterized by the median size of the microcarrier structures within the batch. The actual sizes of the microcarrier structures within the batch typically vary within a normal distribution around the median size. This distribution can be, for example, a distribution in which at least about 90% of the microcarrier structures have a size (such as a diameter or maximum dimension) within about 50 μm to about 300 μm of the median size.

In some embodiments, the median microcarrier structure size is small enough to provide sufficiently enhanced surface area to promote cell activity and large enough to accommodate an optimum number of urokinase-producing cells per microcarrier structure, such as about 100 urokinase-producing cells per microcarrier structure. In several examples, batches of microcarrier structures have median diameters of between about 50 μm and about 300 μm, such as between about 100 μm and about 250 μm or between about 150 μm and about 200 μm. Some microcarrier structures often swell in different media such that their diameter is increased. A batch of swelling microcarrier structures can be selected based on the median size of the microcarrier structures in an environment resembling a typical tissue culture medium, such as a 0.9% NaCl solution.

The effect of microcarrier structures can be enhanced when a greater fraction of the cells attach themselves to the microcarrier structures. Several forces promote this attachment process, including electrostatic forces. Cells typically have a slightly negative surface charge. It therefore is possible to promote attachment by providing microcarrier structures with a slightly positive surface charge.

The microcarrier structures useful for embodiments of the disclosed method can comprise a variety of materials, including, but not limited to, collagen (for example, types I or V), dextran, silica, glass, gelatin, fibrin, fibronectin, laminin, urokinase receptor antibodies, poly-L-lysine, scaffolds (for example, GELFOAM®), and combinations thereof. Some microcarrier structures have a core comprising a first material and a surface comprising a second material. For example, some microcarrier structures are coated with a matrix, such as a matrix comprising collagen (for example, types I or V), and/or urokinase receptor antibodies. Since cells typically attach themselves to an extracellular matrix deposited by other cells, some microcarrier structures mimic the extracellular matrix to promote cell attachment and viability. In one embodiment, the presence of an extracellular matrix facilitates removal of attached cells from the microcarrier structures, which can be accomplished, for example, by introducing proteases.

An example of a microcarrier structure that is well-suited for use with embodiments of the disclosed method and is commercially available is CYTODEX-3, manufactured by Amersham Biosciences (Piscataway, N.J.). CYTODEX-3 microcarrier structures comprise a dextran core and a layer of denatured collagen coupled to the dextran core. CYTODEX-3 microcarrier structures have a density of 1.04 grams/ml, an approximate area of 2700 $cm^2$/gram dry weight, and a swelling factor of 15 ml/gram dry weight. A gram of CYTODEX-3 microcarrier structures contains approximately $3.0 \times 10^6$ individual microcarrier structures. The median diameter of the microcarrier structures in 0.9% NaCl is 175 μm. About 90% of the microcarrier structures have a diameter in 0.9% NaCl between 141 μm and 211 μm.

As described in the examples below, the ratio of urokinase-producing cells to microcarrier structures in the cell culture can effect the production of urokinase. In some of the disclosed examples, enhanced production of urokinase occurred when the cell cultures contained more than 25 urokinase-producing cells per microcarrier structure. In one example, the ratio of urokinase-producing cells to microcarrier structures was between about 75:1 and about 200:1. In another example, the ratio of urokinase-producing cells to microcarrier structures was about 100:1.

D. Cells

A variety of urokinase-producing cells can be used with embodiments of the disclosed method. For example, human renal cells are capable of producing urokinase. Human renal cells can be isolated, for example, from kidneys unsuitable for transplantation. As noted, human cells can be used. Alternatively, non-human animal cells can be used, such as mouse, rat, rabbit, monkey, dog, sheep or goat cells. The cells can be primary cells, such as primary human renal cells. In some embodiments, the cells are immortalized. The cells can be renal cells, but are not limited to renal cells. In one example, non-renal cells are transfected with nucleic acid that encodes urokinase, such as human urokinase. In several embodiments, cells of a cell line can be utilized. These cells include commercially available cells, including both primate and human cells, or cells from other species. In one example, the cells are fibroblasts. Specific non-limiting examples of cells of use include NIH3T3 cells, CHO cells, PC-12 cells, BN cells, and combinations thereof. In the examples below, immortalized human renal cells and immortalized CHO cells transfected with a nucleic acid that encodes urokinase were used. However, the embodiments of the method disclosed herein are not limited to the use of these specific cell types.

E. Other Considerations

In addition to microcarrier structures, the disclosed cell cultures also typically utilize a tissue culture medium. This can be any medium for sustaining the urokinase-producing cells. Suitable components of the tissue culture medium include vitamins, minerals, amino acids, sugars, salts, urokinase receptor antibodies, inhibitors to prevent the breakdown of urokinase (for example, amiloride), and combinations thereof. Such media are well known in the art and are commercially available. One example of a medium well-suited for the growth of urokinase-producing cells is Dulbecco's Modified Eagle's Medium (DMEM), or a mixture of DMEM and F12 (Sigma, St. Louis, Mo.) (such as DMEM/F12 at 1:1). The medium can supplemented with serum, such as fetal calf serum (Life Technologies, Grand Island, N.Y.). Antibiotics also can be added to inhibit the growth of competing microorganisms. A suitable antibiotic cocktail includes ciprofloxacin and fungizone (Life Technologies, Grand Island, N.Y.). Other suitable antibiotics include amoxicillin, penicillin, streptomycin, and combinations thereof.

The components of the disclosed cell cultures can be contained in a variety of vessels. One well-suited vessel is a bag, such as a flexible bag or a flexible bag comprising a fluoropolymer resin, such as TEFLON®. In some embodiments, the vessel includes a material that is resistant to cell attachment. For example, some suitable bags have inner surfaces that resist cell attachment.

Some vessels have gas permeabilities that are advantageous for the production of urokinase. Urokinase-producing cells, like other cells, consume oxygen and release carbon dioxide. Urokinase-producing cells benefit from a continuous supply of oxygen and an elevated concentration of carbon dioxide relative to the surrounding environment, which typically is air. A suitable oxygen concentration in the cell culture is, for example, from about 80% to about 110% of the oxygen concentration of the surrounding environment, or about 20%. A suitable carbon dioxide concentration in the cell culture is, for example, greater than about ten times the carbon dioxide concentration of the surrounding environment, or about 5%.

Some vessels achieve an optimum oxygen concentration by allowing enough oxygen to diffuse into the vessel's interior to replace the oxygen consumed by the urokinase-producing cells. These vessels can be, for example, substantially $O_2$-permeable. Similarly, some vessels achieve an optimum carbon dioxide concentration by retaining some or all of the carbon dioxide produced by the urokinase-producing cells. These vessels can be, for example, substantially $CO_2$-retaining. Vessels that have a low permeability to carbon dioxide and a high permeability to oxygen are advantageous because they facilitate optimal culture conditions without the need for carbon dioxide sensors, oxygen sensors, carbon dioxide supplies, or oxygen supplies.

In several examples, optimum carbon dioxide and/or oxygen concentrations are maintained in the cell culture, such as during the static period, without the use of carbon dioxide and/or oxygen supplies, such as external tanks. In these examples, however, the cell culture can be situated in controlled environments with elevated or decreased carbon dioxide or oxygen concentrations relative to air. Alternatively, the cell culture can be situated in air. In one example, the cell culture is not directly supplied with carbon dioxide from a carbon dioxide supply and the carbon dioxide concentration in the cell culture is greater than about ten times the carbon dioxide concentration in the environment during the static period. In another example, the cell culture is not directly supplied with oxygen from an oxygen supply and the oxygen concentration in the cell culture is from about 80% to about 110% of the oxygen concentration in the environment during the static period.

A suitable vessel is the VUELIFE 30 ml TEFLON® bag #3P-0027 (American Fluoroseal Corp., Gaithersburg, Md.). However, additional vessels can be utilized with the disclosed method, including flasks and bottles. These vessels can be made, for example, from tissue culture plastic, such as a polypropylene or polystyrene, and are commercially available from a variety of sources.

EXAMPLES

The following examples are provided to illustrate certain particular embodiments of the disclosure. It should be understood that additional embodiments not limited to the particular features described are consistent with this disclosure.

These examples describe experiments that were performed to investigate the effect of different cell culture conditions on the production of urokinase. The production of urokinase, dihydroxyvitamin D-3, and other renal products in generally static cell cultures (those cultures without substantial mixing) was compared to the production of urokinase, dihydroxyvitamin D-3, and other renal products in cell cultures subjected to a variety of mechanical stimuli. The tested mechanical stimuli included actual microgravity (achieved by subjecting the cell cultures to space flight), simulated microgravity (achieved by culturing the cells in a specially designed rotating wall vessel), vibration, and centrifugation. The results demonstrate that the production of urokinase, in contrast to the production of dihydroxyvitamin D-3, was enhanced when the cell cultures were not subjected to the various types of mechanical stimuli tested.

I. Selection and Preparation of Cells

Most of the experimental trials were performed with primary human renal cortical cells. Isolated human renal cortical cells from kidneys unsuitable for transplantation are available from Clonetics Inc. of San Diego, Calif. Before culturing, the cell fractions mirrored the natural mixture of cells in the renal cortex. The cells were >99% proximal tubular cells judged by flow cytometry assay of the proximal tubular enzyme markers γ-glutamyl-transpeptidase and leucine aminopeptidase following passage in selective culture media.

In the experimental trials directed to the optimization of the cell-to-microcarrier-structure ratio, CHO cells were used as the urokinase-producing cell line. The CHO cells were grown in parallel using DMEM/F12 medium supplemented with 2% fetal calf serum and antibiotics.

The primary human renal cells were transformed with a nucleic acid encoding the Simian Virus 40 (SV40) large T antigen (Tag) to immortalize the cells. See Chen, C., and Okayama, H., *High-Efficiency Transformation of Mammalian Cells by Plasmid DNA,* 7 Mol. Cell. Biol. 2745-2752 (1987). Briefly, exponentially growing cells were trypsinized, seeded at $5 \times 10^6$ cells per 10-cm plate, and incubated overnight in 10 ml of medium. The cells were inoculated with 20-30 μg of plasmid SV2 Neo or SV3 Neo DNA (American Type Culture Collection, Manassas, Va.) and mixed with 0.5 ml of a 0.25 M $CaCl_2$ solution and then added to 0.5 ml of a 2× concentration of BBS (Sigma, St. Louis, Mo.). The mixture was incubated for 10-20 minutes at room temperature with the hood lights off. Calcium phosphate-DNA solution (1 ml) was added dropwise to the plate of cells and swirled gently. The samples then were incubated for an additional 4-24 hours at 35-37° C. under 2-6% $CO_2$. The medium was removed, and the cells were rinsed twice in the growth medium, refed, and incubated for 24 hours at 35-37° C. under 5-6% $CO_2$. The cells were subcultivated at (>1:10) and incubated for an additional 24 hours before stable transformants were selected.

Transfected cells were subcultivated and plated at $10^3$ cells per 10-cm plate 24 hours before selection. The transfected cell cultures were verified by immunohistochemical staining with a mouse monoclonal antibody (working dilution 1:250) generated against SV40 Tag (Chemicon International, Temucula, Calif.).

II. Preparation of the Cell Cultures

To initiate the cell cultures, vessels were seeded with a solution containing $1 \times 10^6$ cells/ml cell suspension. The medium used was DMEM/F12 (Sigma, St. Louis, Mo.) supplemented with 10% fetal calf serum (Life Technologies, Grand Island, N.Y.), and an antibiotic cocktail comprising ciprofloxacin and fungizone (Life Technologies, Grand Island, N.Y.). Concomitant with the cells, CYTODEX-3 microcarrier beads (Sigma, St. Louis, Mo.) were added at 5 mg/ml to promote aggregate formation. All of the cultures were derived from aliquots of the same stock of cells.

Feeding, seeding, and duration were identical for each experimental trial. Primary human renal cells grow relatively slowly, so it was possible to perform the experiment without substantial refeeding. For the space flight and short arm centrifuge experiments, the cell cultures were contained in VUELIFE FEP 30 ml TEFLON® bags #3P-0027, which are $CO_2$ retaining and $O_2$ permeable (American Fluorseal Corp, Gaithersburg, Md.).

III. Culture Conditions

One of the mechanical culture conditions tested was actual microgravity. Human renal cells were flown on Space Transportation System flight 106 (STS-106) using flight hardware supplied by BioServe, University of Colorado. The flight hardware provided thermal control and automatic execution of experiments. The cells were cultured in four separate 30 ml bags incubated in a BioServe Culture Apparatus (BCA). The bags each were filled with 14 ml of cells on CYTODEX-3 microcarrier beads. Two Alzet osmotic pumps model 2001 (1 μl/h, 7 days) (Durect, Inc, Cupertino, Calif.) filled with 200 μl of 50% glucose were placed inside the bags. This eliminated the need to re-feed the cells after loading them. Two hours after launch, 4 ml cell culture samples were drawn into vacutainers containing a mix of phosphatase and protease inhibitors (Sigma, St. Louis, Mo.) and sodium azide to stabilize proteins. Ten ml of RNA later (Ambion, Austin, Tex.) was injected into each bag to protect the cellular RNA and eliminate the need to immediately process or freeze the samples. The cells remained at 7° C. for the remainder of the flight. After return to Earth, the samples were transported at 4° C. back to Tulane University where the RNA was extracted using Trizol Reagent (Life Technologies, Grand Island, N.Y.).

In an attempt to identify the effect of different mechanical culture conditions, several mechanical culture conditions typically associated with space flight were tested in isolation. N=4 for each tested condition.

Some cell cultures were tested after exposure to a vibration profile similar to the vibration profile characteristic of a space shuttle launch. The vibration parameters were as follows: 20 Hz (0.00054 g 2/Hz, 20-150 Hz @+6.0 dB/oct, 150-1000 Hz (0.03 $g^2$/Hz, 1000-2000 Hz @-6.0 dB/oct, 2000 Hz (0.0075 $g^2$/Hz, Composite=6.5 g root mean square.

Other cell cultures were exposed to the high g-force characteristic of space shuttle launch. The cells were centrifuged in a Genisco centrifuge model 1230-5, which was designed to hold large items. The centrifugation was performed for 8 minutes at 3 g.

Some cells were cultured in a rotating wall vessel. The rotating wall vessel included a 10 ml horizontally rotating cylindrical vessel (Synthecon Inc., Houston, Tex.) and a co-axial tubular oxygenator. The system was designed to simulate the true microgravity of space by facilitating suspension of the culture with minimum shear and turbulence. Residual air was removed through a syringe port and vessel rotation was initiated at 17 rotations per minute.

Finally, in contrast to the other cell cultures, the substantially static cell cultures, sometimes also referred to herein as "bag controls" or "ground controls," were allowed to sit without substantial mixing. These cultures were not subjected to any intentional mixing or agitation, and were allowed to sit undisturbed during the static period. Hence, any mixing or agitation only occurred from incidental, ambient, or inadvertent, minor movements.

IV. Quantifying Gene Expression

A 10 mg sample of total RNA was converted into double stranded cDNA (ds-cDNA) by using SuperScript Choice System (Life Technologies, Grand Island, N.Y.) with an oligo-dT primer containing a T7 RNA polymerase promoter (Genset, San Diego, Calif.). After second-strand synthesis, the reaction mixture was extracted with phenol-chloroform-isoamyl alcohol, and ds-cDNA was recovered by ethanol precipitation.

In vitro transcription was performed on the above ds-cDNA using the Enzo RNA transcript Labeling Kit (Farmingdale, N.Y.). Biotin-labeled cRNA was purified with an RNeasy affinity column (Qiagen, Valencia, Calif.), and fragmented randomly to sizes ranging from 35-200 bases by incubating at 94° C. for 35 minutes. The hybridization solutions contained 100 mM MES, 1 M $Na^+$, 20 mM EDTA, and 0.01% Tween 20. The final concentration of fragmented cRNA was 0.05 mg/ml in the hybridization solution.

The target for hybridization was prepared by combining 40 ml of fragmented transcript with sonicated herring sperm DNA (0.1 mg/ml), BSA and 5 nM control oligonucleotide in a buffer containing 1.0 M NaCL, 10 mM Tris-HCl (pH 7.6), and 0.005% Triton X-100. The target was hybridized for 16 hours at 45° C. to a set of oligonucleotide arrays (Affymetrix, Santa Clara, Calif.). The arrays were washed at 50° C. with stringent solution, then at 30° C. with non-stringent washes. The arrays then were stained with streptavidin-phycoerythrin (Molecular Probes, Eugene, Oreg.). The DNA chips were read at a resolution of 3 mm with a Hewlett-Packard GeneArray Scanner and were analyzed with GENECHIP software (Affymetrix, Santa Clara, Calif.).

Detailed protocols for data analysis of Affymetrix microarrays and extensive documentation of the sensitivity and quantitative aspects of the method are described in D. J. Lockhart et al., *Expression Monitoring by Hybridization to High-Density Oligonucleotide Arrays,* 14 Nat. Biotechnol. 1675-1680 (1996). Briefly, each gene is represented by the use of about 20 perfectly matched (PM) and mismatched (MM) control probes. The MM probes act as specificity controls that allow the direct subtraction of both background and cross-hybridization signals. The number of instances in which the PM hybridization signal is larger than the MM signal is computed along with the average of the logarithm of the PM:MM ratio (after background subtraction) for each probe set. These values are used to make a matrix-based decision concerning the presence or absence of an RNA molecule. Comparison analysis between control and experimental animals were made with Affymetrix software.

The data was loaded into GeneSpring software version 4.0 (Silicon Genetics, Palo Alto, Calif.). Analysis methods known as principal component analysis (PCA), K-means, and self-organizing maps (SOM) were applied along with different mathematical algorithms (Standard Correlation, Pearson Correlation, and Spearman Correlation) to identify changes in gene cluster expression. The analysis of the data was designed to first separate the genes into lists according to their change in expression (up or down) in comparison with the control. Further information about the analysis methods can be found in A. Brazma and J. Vilo *Gene Expression Data Analysis,* 480 FEBS Lett. at 17-24 (2000); M. B. Eisen et al., *Cluster Analysis and Display of Genome-Wide Expression Patterns,* 95 PNAS USA 14863-14868 (1998); J. Quackenbush, *Computational Analysis of Microarray Data,* 2 Nat. Rev. Genet. 418-427 (2001); G. Sherlock, *Analysis of Large-Scale Gene Expression Data,* 12 Curr. Opin. Immunol. 201-205 (2000); and P. Tamayo et al., *Interpreting Patterns of Gene Expression with Self-Organizing Maps: Methods and Application to Hematopoietic Differentiation,* 96 PNAS USA 2907-2912 (1999).

PCA explores the variability in gene expression and searches for genes that have correlated patterns of expression. The first principal component is obtained by finding the linear combination of expression patterns explaining the greatest amount of variability in the data. The second principal component is obtained by finding another linear combination of expression patterns that is not correlated with the first principal component. Each succeeding principal component is similarly obtained.

K-means clustering divides genes based on expression patterns using Standard, Pearson or Spearman correlations to define clusters. The Standard correlation measures the angular separation of expression vectors for Genes A and B around zero. The Pearson correlation measures the angle of expression vectors for genes A and B around the mean of the expression vectors. The Spearman correlation is a nonparametric correlation that replaces the data for Gene A and B by the ranks of the data. It calculates the correlation of the ranks for Genes A and B's expression data around the mean of the ranks, using the same formula as the Pearson correlation.

Self-organizing maps use an Euclidian non-linear metric system. Each cluster is distinct. The arrangement of clusters is significant in that the closer clusters appear to each other in the spatial map, the more similar they are to each other. The strength of the cluster analysis can be validated in three ways. First, the percent variability explained by the analysis should be high (>80%). Second, repeat analysis of the genes in each individual cluster should not indicate a further increase in percent variability of the overall analysis. Third, the various methods should give similar results, with similar clusters of genes observed with each form of analysis.

V. Quantifying 1,25-dihydroxyvitamin D and Urokinase in the Cell Cultures 1,25-dihydroxyvitamin D in the cell cultures was quantified by radioimmunoassay (RIA). The RIA for 1,25-dihydroxyvitamin D utilized a radioiodinated (125I) tracer. The assay involved acetonitrile extraction, treatment of the crude extract supernate with sodium periodate, extraction and purification of endogenous $1,25(OH)_2D$ by solid-phase chromatography, and finally, quantification by RIA. The detection limit of the assay was 2.4 ng/L 1,25-dihydroxyvitamin D3. Additional details about this process can be found in B. W. Hollis, *Quantitation of 25-hydroxyvitamin D and 1,25-dihydroxyvitamin D by Radioimmunoassay Using Radioiodinated Tracers,* 282 Methods Enzymol. 174-186 (1997) and B. W. Hollis et al., *Quantification of Circulating 1,25-dihydroxyvitamin D by Radioimmunoassay with* 125I-labeled Tracer, 42 Clin. Chem. 586-592 (1996)

An enzyme-linked immunosorbent assay (ELISA) was utilized for the measurement of urokinase-type plasminogen activator (u-PA) (American Diagnostics, Greenwich, Conn.). The lower limit of sensitivity of the assay was 1 ng/ml in plasma. Statistical analysis was performed using InStat 3.0 for Macintosh (GraphPad Software, San Diego, Calif.). One-way analysis of variance and unpaired two-tailed t tests were applied to obtain the mean, standard error of the mean, and P values for replicate samples. Statistical significance was considered to be $P \leq 0.05$. Additional details about this process can be found in F. Buessecker et al., *Enzyme-Linked Immunosorbent Assays for Plasminogen Activators,* 162 J. Immunol. Methods 193-200 (1993) and V. Darras et al., *Measurement of Urokinase-Type Plasminogen Activator (u-PA) with an Enzyme-Linked Immunosorbent Assay (ELISA) Based on Three Murine Monoclonal Antibodies,* 56 Thromb. Haemost. 411-414 (1986).

VI. Results—Gene Expression

Metabolic test were performed using an i-Stat (i-Stat Corporation, East Windsor, N.J.). The data suggests that each group of cell cultures grew at a similar rate: glucose fell 30 mg/ml/day, BUN rose 0.5 mg/ml/day and pH was maintained between 7.31 and 7.34. Oxygenation was excellent in all cultures with $pO_2$ 155-167 mmHG for 99% saturation, $pCO_2$ 12-13 mmHg, and $HCO_3$ 6-6.6 mmol/L.

Comparison of gene expression between different culture conditions was done using GeneSpring software (Silicon Genetics, Palo Alto, Calif.). The results are shown in FIG. 1A. To compare patterns of gene expression, all cultures were compared to gene expression in the ground control, with the same genes shown in a column as bars from top to bottom with dark grey intensity representing degree of decrease in each gene, and light grey intensity the degree of increase in each gene. Venn Diagrams, such as the one illustrated in FIG. 1B, were used to compare the different conditions and generate gene lists. FIG. 1A illustrates clear differences in gene up-regulation and down-regulation by the different culture conditions. Examples of the genes differentially expressed by the different culture conditions can be found in Table 1.

TABLE 1

Gene Lists

| Centrifuge | Ground |
|---|---|
| Guanine nucleotide binding protein | Calbindin 1 |
| 3',5'-cyclic GMP phosphodiesterase | Phospholipase C, gamma 2 |
| Cytochrome P450IIF HEK7 | Cytochrome P450IIIA |
| HEK7 | EphA5 |
| Centromere protein E | Proteoglycan 4 |
| Dystrobrevin | XIAP associated factor-1 |
| Apolipoprotein L | Centrin |
| translation initiation factor 1A | Myosin-binding protein C |
| Hexokinase 2 | Calpain 5 |
| ZYG homolog | Apolipoprotein A-I |
| RAP2A | cytochrome P450IIA3 |
| Phospholipase A2 | KIF3X |
| DR1-associated protein 1 | IGFBP-2 |
| aquaporine 3 | RAB3A |
| NRAMP1 | Cytochrome P450IVF |
| Dynein | TGF beta 1 |
| Cytochrome P450XIB | Cyclin T2 |
| Diacylglycerol kinase q | GRF-1 |
| TGF beta-3 | FAP |
| ALK-1 | Caspase 1 |

| Vibration | Flight | RWV |
|---|---|---|
| Dynactin 1 | Cyclin-dependent | alkalin phosphatase |
| Syk | kinase-like 1 | apolipoprotein D |
| DP-1 | alpha-catenin | SMA5 |
| JAK1 | Apoptosis inhibitor 5 | Nuclear factor I/X |
| SAPK4 | Cyclin T1 | Villin 1 |
| MLC-3 | Crystallin, beta B1 | ABC1 |
| PEX1 | Caspase 10 | TEF1 |
| nitric oxide synthase | Keratin 17 | G protein beta |
| Tropomyosin 1 (alpha) | Centromere protein B | COL4A2 |
| P kinase C, iota | Nef-associated factor 1 | COL11A2 |
| Jun D | SKIP | Relaxin 1 |
| NF-kappa-B | Spectrin | Keratin 15 |
| BAII-associated protein 1 | GAPDH | Ankyrin 1 |
| Coronin | Profilin 1 | Fibrinogen, gamma |
| Endoglin | Cytochrome P450IIE | Relaxin 1 |
| Cyclin-dependent kinase 4 | ERCC1 | NEC2 |
| Topoisomerase I | Caspase 7 | Melastatin 1 |
| CHK1 | NPAT | hsp110 |
| Topoisomerase II alpha | RP1 | Integrin, beta 4 |
| E2F transcription factor 4 | 25-OH Vit D3 1-a-OHase CYB5 | Genethonin 1 |

Following the comparison of expression between different culture conditions, pattern analyses were performed. The first analysis performed was the principal component analysis (PCA). FIG. 1C illustrates a PCA gene cluster. Each point represents a set of genes being expressed at each condition. The PCA indicated five different sets of gene expression and showed substantial differences in expression patterns between the various culture conditions.

Subsequent to the PCA, a K-means analysis was performed. K-means clustering divides the genes into distinct groups based on expression pattern. Genes are reassigned to the group with the highest similarity between the expression profile for the gene and the group. FIG. 1D illustrates the resulting K-means. Unlike in the PCA where color bars indicated the level of confidence, K-means color bars represent a cluster of genes. A representative list of genes present in each cluster is shown in Table 2.

TABLE 2

K-means Clusters

| Cluster 1 | Cluster 2 | Cluster 3 | Cluster 4 | Cluster 5 |
|---|---|---|---|---|
| CYP1 | CYP 2C | ERK1 | SMAD5 | TRAF6 |
| hCox-2 | SAPK2 | BLR1 | IFNG | RAD6B |
| CYP1A2 | HSPA1L | PKCI-1 | TFIIB | HEK2 |
| PLC1 | MART-1 | E2F-5 | CDK8 | JAK1 |
| EPOR | GATA-2 | HIF-1a | VLA1 | HEK11 |

Clusters generated by K-means were subjected to self-organizing map (SOM) analysis. FIG. 1E shows a SOM superimposed on the k-means. Each small graph represents similarly expressed genes in response to the culture conditions. The effect of the culture conditions on gene expression are represented by the position of the graph on the map. In the SOM analysis, each cluster is distinct and the arrangement of clusters is significant as well. The closer the clusters appear to each other in the spatial map, the more similar they are to each other. A list of genes included in some of the SOM clusters is shown in Table 3.

TABLE 3

SOM Cultures

| SOM 1, 1 | SOM 2, 2 | SOM 3, 3 | SOM 4, 4 | SOM 5, 5 |
|---|---|---|---|---|
| NFKB3 | MEK2 | EIF2 | SP1 | CYP1A2 |
| HIF-1a | MAPKK1 | PKCM | KBF1 | DAGK3 |
| IEX-1 | KIP | CYP2A3 | CYP4F | IFNB |
| EEF1A | HSP90-b | DDR3 | TCF3 | TSP1 |
| HC7-I | CRABP-II | SMAD2 | KBF1 | NF1 |

Each single graph in the SOM represents the intensity of expression from one to five in the Y-axis and the number of genes expressed in the X-axis. A close up of a single graph in the SOM is shown in FIG. 1F.

VII. Results—Renal Products

In addition to gene expression, the functional production of renal products, including 1-25-dihydroxyvitamin D3 and urokinase, was observed for cells cultured under the various experimental culture conditions. The results then were compared to the predicted results based on the gene expression patterns.

Figure 2:
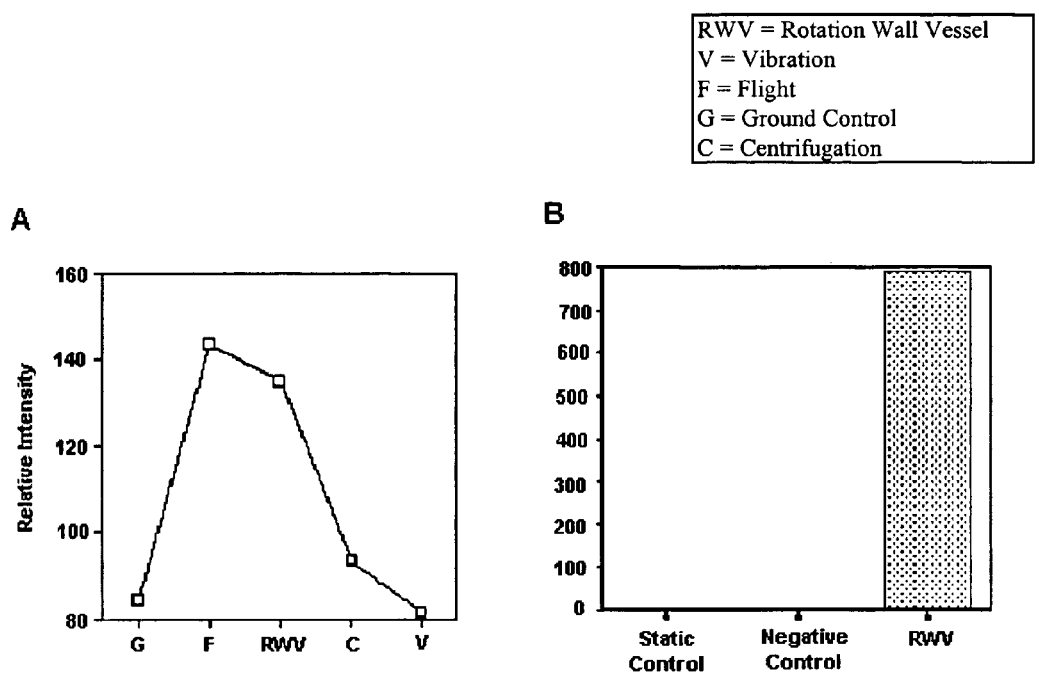
FIGS. 2A and 2B are a line graph (FIG. 2A) and a bar graph (FIG. 2B) that illustrate the production of 1-25-dihydroxyvitamin D3 1-alpha hydroxylase by human renal cortical cells subjected to different mechanical culture conditions.

The active 1-25-dihydroxy form of vitamin D3 is made in the kidney by the enzyme 1-alpha-25-hydroxylase. Maintenance of this activity in cell culture has been a major impediment to studies of its renal regulation. See, for example, K. Takeyama et al., 25-*Hydroxyvitamin D3 1-alpha-hydroxylase and Vitamin D Synthesis,* 277 Science 1827-1830 (1997). Nevertheless, as seen in FIG. 2A, the gene array profile of 1-alpha-25-hydroxylase suggests abundant expression during both rotating wall vessel culture and flight, but not during other mechanical culture conditions.

To test whether the rotating wall vessel and flight provided functional 1-alpha-25-hydroxylase activity, a classic assay for this enzyme activity was performed. Primary renal cells were cultured for 24 hours on beads in a stationary culture bag or rotating wall vessel and were exposed to 10 mM 25-OH vitamin D3 as substrate. The 1-25-dihydroxyvitamin D3 produced in 6 hours was assayed by double antibody radioimmunoassay techniques, as discussed above. As evidenced by 1-25-dihydroxyvitamin D3 production, the rotating wall vessel culture of renal cells was associated with abundant 1-alpha-25-hydroxylase functional activity not seen in the bag controls or in rotating wall vessel grown cells boiled to denature the enzyme. These results are summarized in FIG. 2B.

The pattern of expression of the urokinase demonstrates the unexpected superiority of the stationary culture method. Unlike the pattern for 1-alpha-25-hydroxylase, which was high in the suspension culture conditions, urokinase production was highest in the stationary bag controls with cells on beads, lowest in flight, and modest in the centrifuge and vibration cultures. The results are provided in FIG. 3A. The unexpectedly high production of urokinase in the stationary bag controls demonstrates the superiority of producing urokinase under stationary culture conditions, without external application of agitation or mechanical disruption of the culture milieu. The production of urokinase, when compared to the production of 1-alpha-25-hydroxylase and other renal products, also demonstrates that the optimal mechanical culture conditions vary widely for the production of different renal products.

To further test the impact of culture conditions on the production of urokinase, the urokinase in the experimental cell cultures was assayed by a monoclonal antibody based ELISA. Compared to the media, the urokinase demonstrated some increased activity in the conventional two-dimensional culture (labeled "Flask" in FIG. 3B) and the rotating wall vessel, but it was far greater for the cells grown in bags on beads without substantial mixing. See FIG. 3B. The same pattern was observed when immortalized renal proximal tubular cells were used instead of the primary cultures.

To further investigate the production of urokinase in an immortalized renal cell system, a time course was performed. The time course showed that a near steady state was achieved at 24 hours. See FIG. 3C.

Figure 3:
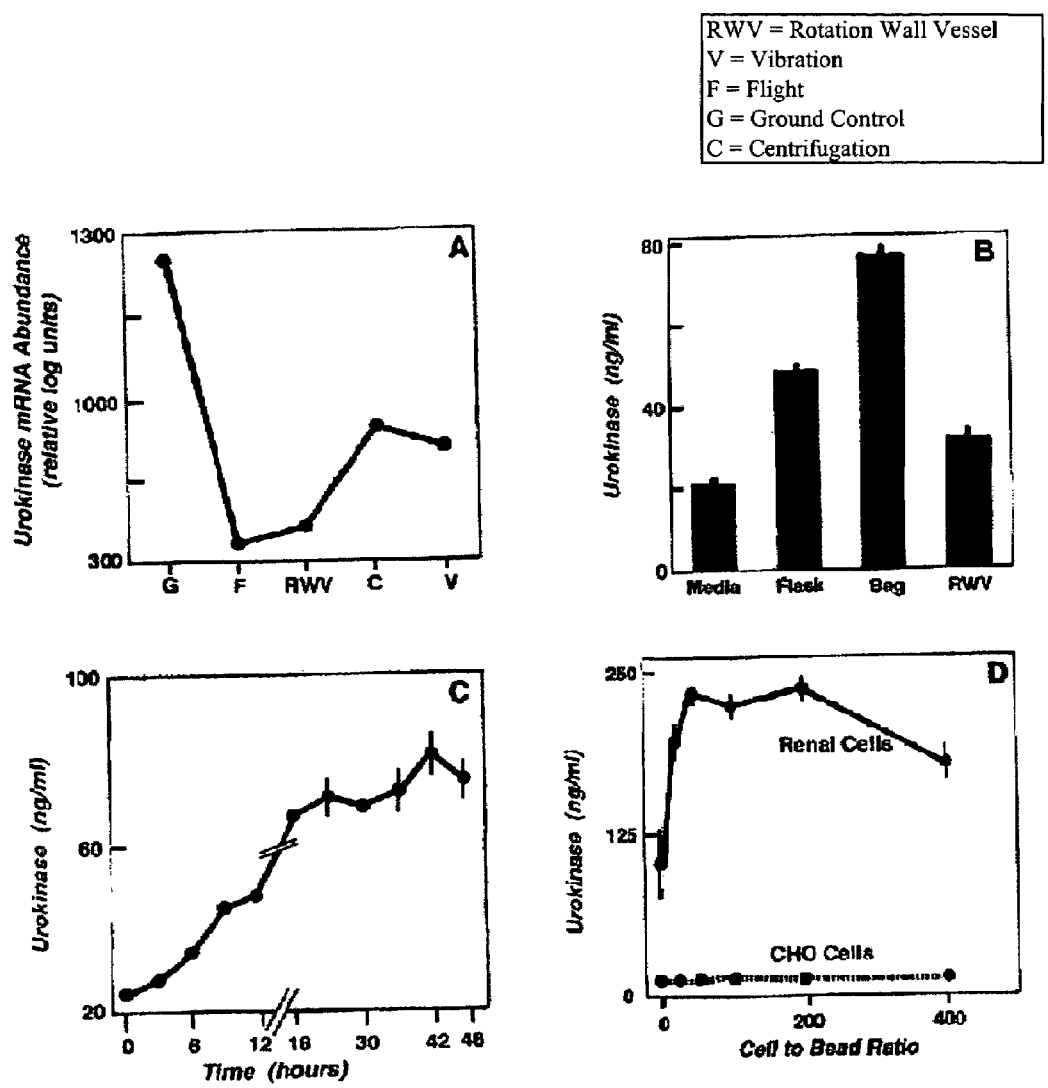
FIGS. 3A and 3B are a line graph (FIG. 3A) and a bar graph (FIG. 3B) that illustrate the production of urokinase by human renal cortical cells subjected to different mechanical culture conditions.
FIG. 3C is a time course plot illustrating the production of urokinase by human renal cortical cells over a 48 hour period.
FIG. 3D is a line graph of urokinase production by CHO cells and human renal cortical cells versus cell-to-microcarrier-structure ratio in the cell culture.

As shown in FIG. 3D, the optimum ratio of cells to microcarrier structures was also determined. A broad optima can be seen centered on a 1:100 cell-to-microcarrier-structure ratio. To allow comparison of production levels of urokinase to a cell line commonly used for urokinase regulation studies, CHO cells were grown in parallel to renal cells for this part of the experiment. The production of urokinase by CHO cells, while detectable, was more than two orders of magnitude less than the production by immortalized renal cells. See FIG. 3D.

In addition to 1-25-dihydroxyvitamin D3 and urokinase, several other renal products were studied. Analysis of 20 genes showing expression changes specifically restricted to each individual mechanical condition showed that each culture condition is characterized by specific changes in heterotromeric G-protein isoforms, cytoskeletal proteins, MAP kinases, cytochrome P450s, phospholipases, transcription factors, and receptors, among other genes.

Figure 4:
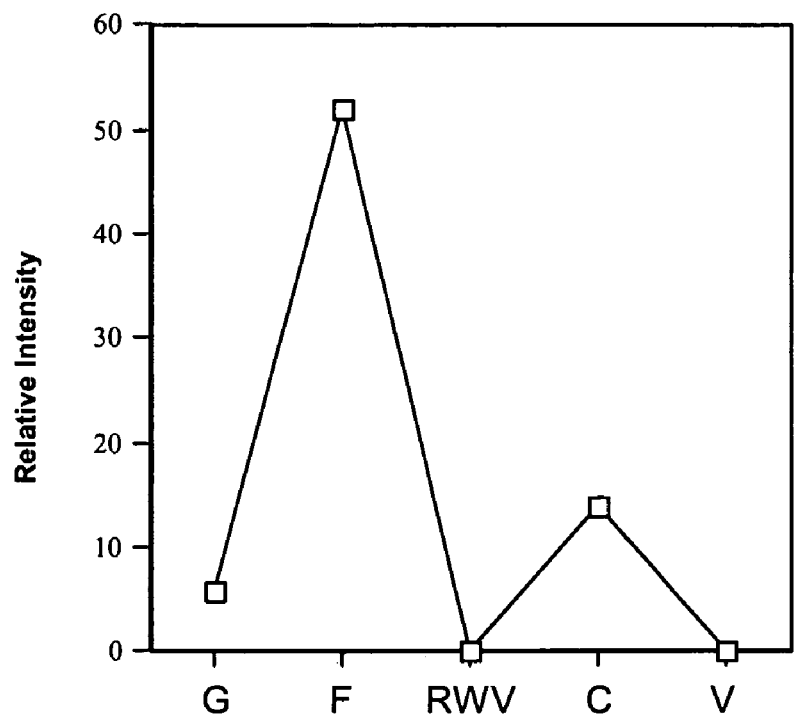
FIG. 4 is a line graph of interferon-gamma gene expression by human renal cortical cells subjected to different mechanical culture conditions.
Figure 5:
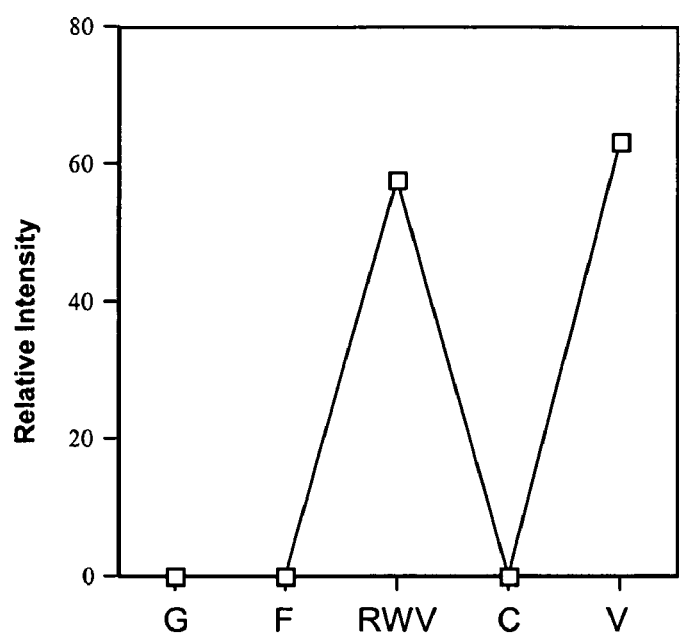
FIG. 5 is a line graph of parathyroid hormone gene expression by human renal cortical cells subjected to different mechanical culture conditions.
Figure 6:
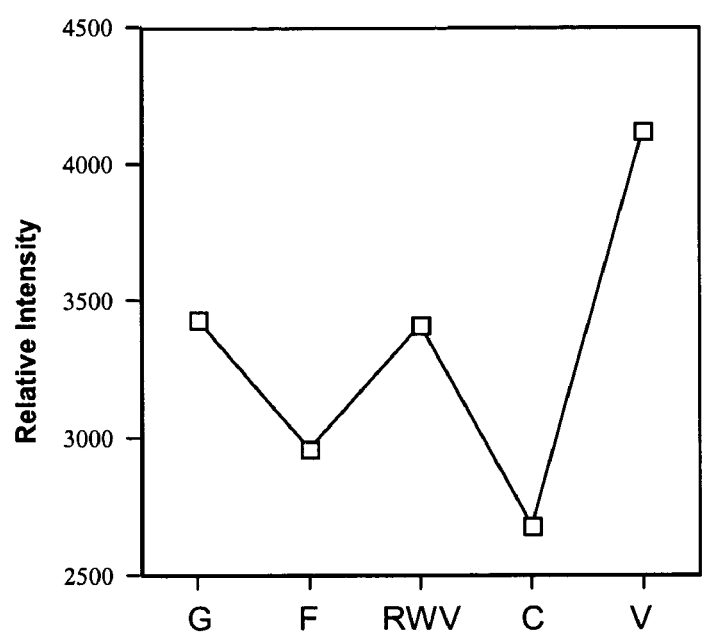
FIG. 6 is a line graph of osteopotin gene expression by human renal cortical cells subjected to different mechanical culture conditions.
Figure 7A:
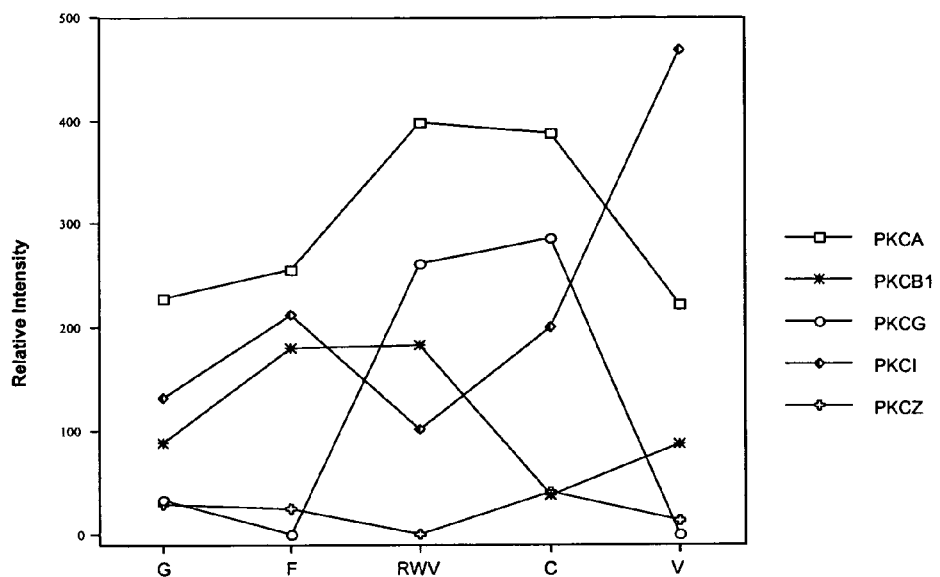
FIG. 7 is a line graph of protein kinase C gene expression by human renal cortical cells subjected to different mechanical culture conditions.
Figure 7B:
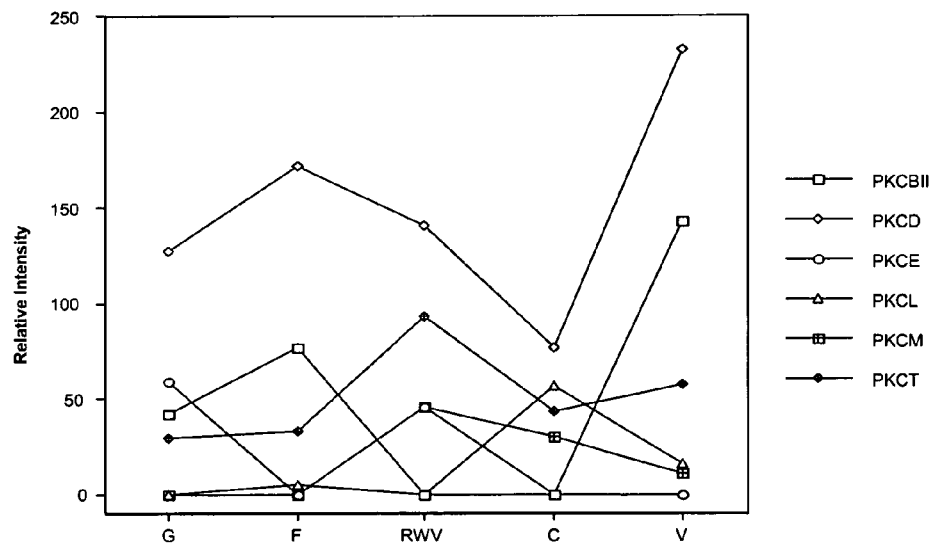
Figure 8:
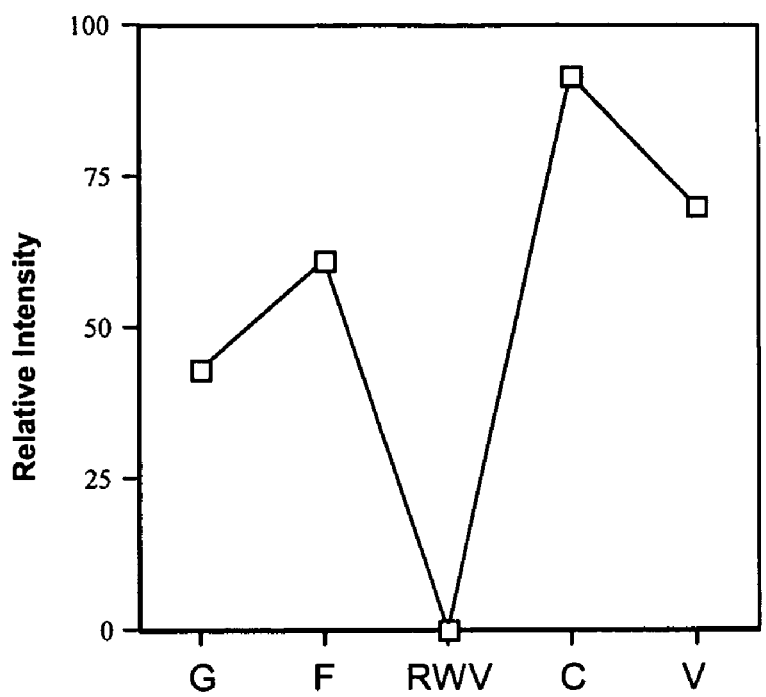
FIG. 8 is a line graph of nitric oxide synthase gene expression by human renal cortical cells subjected to different mechanical culture conditions.

No erythropoietin gene expression was detected in any of the culture conditions. Interferon-gamma gene expression demonstrated a distinct pattern, with highest expression in the flight samples, modest expression in the centrifuge samples, and no detectable expression elsewhere. See FIG. 4. Abundant expression of parathyroid hormone (PTH) was observed for the rotating wall vessel cultures and the cell cultures subjected to vibration, but not for the cell cultures subjected to the other mechanical culture conditions. See FIG. 5. Abundant expression of osteopotin was observed for the cell cultures subjected to vibration, but not for the cell cultures subjected to the other mechanical culture conditions. See FIG. 6. The gene expression of each of the ten known isoforms of protein kinase C(PKC) responded differently to different mechanical culture conditions. See FIGS. 7A and 7B. Finally, abundant expression of nitric oxide synthase (iNOS) was observed for the cell cultures subjected to centrifugation and the cell cultures subjected to vibration. Abundant expression of iNOS also was seen in flight. This was likely due to the vibration experienced during launch.

Other embodiments of the invention will be apparent to those of ordinary skill in the art from a consideration of this specification, or practice of the invention disclosed herein. It is intended that the specification and examples be considered as exemplary only, with the true scope and spirit of the invention being indicated by the following claims.

We claim:

1. A method for the production of human urokinase, comprising: culturing urokinase-producing cells in a cell culture comprising a plurality of microcarrier structures and a tissue culture medium for a culture period, where the urokinase-producing cells are cultured in static culture conditions without substantial mixing for a portion of the culture period sufficient to cause enhanced urokinase production; and isolating human urokinase from the cell culture.

2. The method of claim 1, where the portion of the culture period is greater than about three hours.

3. The method of claim 1, where the shear stress within the cell-culture during the portion of the culture period is less than about 0.1 dynes/cm2.

4. The method of claim 1, where the urokinase-producing cells are human renal cells.

5. The method of claim 4, where the human renal cells are immortalized.

6. The method of claim 1, where the cell culture is contained within a flexible bag.

7. The method of claim 6, where the flexible bag is substantially CO2-retaining and substantially O2-permeable.

8. The method of claim 6, where the flexible bag comprises a fluoropolymer resin.

9. The method of claim 1, where the cell culture is contained within a vessel, the vessel has an interior surface, and the interior surface is resistant to cell attachment.

10. The method of claim 1, where the cell culture is separated from an environment by a vessel, the carbon dioxide concentration in the cell culture is greater than ten times the carbon dioxide concentration in the environment during the portion of the culture period where the cells are cultured under static conditions, and the cell culture is not supplied with carbon dioxide from a carbon-dioxide supply.

11. The method of claim 1, where the cell culture is separated from an environment by a vessel, the oxygen concentration in the cell culture is from about 80% to about 110% of the oxygen concentration in the environment during the portion of the culture period where the cells are cultured under static culture conditions, and the cell culture is not supplied with oxygen from an oxygen supply.

12. The method of claim 1, where the tissue culture medium comprises fetal calf serum.

13. The method of claim 1, where at least about 90% of the microcarrier structures have a median diameter of between about 50 gm and about 300 gm.

14. The method of claim 1, where the surface of one or more of the microcarrier structures comprises collagen.

15. The method of claim 14, where the collagen is chemically coupled to a microcarrier-structure core and the microcarrier-structure core comprises dextran.

16. The method of claim 1, where the ratio of urokinase-producing cells to microcarrier structures in the cell culture is greater than about 25:1 and less than about 500:1.

17. The method of claim 1, where the ratio of urokinase-producing cells to microcarrier structures in the cell culture is greater than about 75:1 and less than about 200:1.

18. The method of claim 1, where the ratio of urokinase-producing cells to microcarrier structures in the cell culture is about 100:1.

19. A method for the production of human urokinase, comprising: culturing immortalized human renal cells in a cell culture comprising a plurality of microcarrier structures and a tissue culture medium for a culture period, where the immortalized human renal cells are cultured in static culture conditions without substantial mixing for a portion of the culture period greater than about three hours, and the ratio of human renal cells to microcarrier structures in the cell culture is greater than about 25:1 and less than about 500:1; and isolating human urokinase from the cell culture.

20. The method of claim 19, where the surface of one or more of the microcarrier structures comprises collagen.

21. The method of claim 19, where the cell culture is contained within a flexible bag.

22. The method of claim 21, where the flexible bag is substantially $CO_2$-retaining and substantially $O_2$-permeable.

* * * * *

UNITED STATES PATENT AND TRADEMARK OFFICE
CERTIFICATE OF CORRECTION

PATENT NO.         : 7,361,493 B1                                              Page 1 of 1
APPLICATION NO. : 11/139102
DATED              : April 22, 2008
INVENTOR(S)       : Hammond and Allen It is certified that error appears in the above-identified patent and that said Letters Patent is hereby corrected as shown below:

Column 4, line 34, "$HC_{7-1}$" should read --HC7-1--.
Column 4, line 51, "KBF," should read --KBF1--.
Column 5, line 1, "(NF1 A)" should read --NF1A--.
Column 5, line 36, "$TCF_3$" should read --TCF3--.
Column 8, line 41, "Static Period" should read --Static Period:--.
Column 10, line 47, "$\mu M$" should read --Am--.
Column 16, line 23, "(0.0075 $g^2$/Hz," should read --@ 0.0075 $g^2$/Hz,--.

In the Claims:
Col. 22, claim 7, line 34, "CO2-retaining" should read --$CO_2$-retaining--.
Col. 22, claim 7, line 34, "O2-permeable" should read --$O_2$-permeable--.
Col. 22, claim 13, line 59, "50 gm and about 300 gm." should read --50 μm and about 300 μm.--.
Col. 24, claim 22, line 10, "CO2-retaining" should read --$CO_2$-retaining--.
Col. 24, claim 22, line 10, "O2-permeable" should read --$O_2$-permeable--.

Signed and Sealed this

Twenty-fourth Day of March, 2009

JOHN DOLL
*Acting Director of the United States Patent and Trademark Office*